US008863567B2

(12) United States Patent
Jappy et al.

(10) Patent No.: US 8,863,567 B2
(45) Date of Patent: Oct. 21, 2014

(54) METHOD AND APPARATUS FOR FLUID LOSS MEASUREMENTS OF WELLBORE FLUIDS

(75) Inventors: Trevor G. Jappy, Aberdeen (GB); Lynn H. Jenkins, Aberdeen (GB); Mark W. Sanders, Banchory (GB)

(73) Assignee: M-I L.L.C., Houston, TX (US)

( * ) Notice: Subject to any disclaimer, the term of this patent is extended or adjusted under 35 U.S.C. 154(b) by 0 days.

(21) Appl. No.: 12/674,258

(22) PCT Filed: Aug. 20, 2008

(86) PCT No.: PCT/US2008/073712
§ 371 (c)(1),
(2), (4) Date: Feb. 19, 2010

(87) PCT Pub. No.: WO2009/029451
PCT Pub. Date: Mar. 5, 2009

(65) Prior Publication Data
US 2011/0290012 A1    Dec. 1, 2011

(51) Int. Cl.
*G01N 15/00*    (2006.01)
*B01D 35/28*    (2006.01)

(52) U.S. Cl.
USPC ........................................... 73/61.64

(58) Field of Classification Search
USPC .................. 210/346, 418, 473, 482
See application file for complete search history.

(56) References Cited

U.S. PATENT DOCUMENTS

| | | | | |
|---|---|---|---|---|
| 1,021,133 | A | * | 3/1912 | Chaloud, Jr. ............... 99/418 |
| 1,471,361 | A | * | 10/1923 | Sarles ............... 209/372 |
| 2,449,238 | A | * | 9/1948 | Lightfoot, Jr. ............... 210/232 |
| 2,455,486 | A | * | 12/1948 | Hicks ............... 210/492 |
| 2,547,797 | A | * | 4/1951 | Torrey et al. ............... 210/445 |
| 2,618,151 | A | * | 11/1952 | Leas ............... 73/38 |
| 2,646,678 | A | * | 7/1953 | Standing et al. ............... 210/455 |
| 2,733,595 | A | * | 2/1956 | Twining ............... 73/38 |
| 2,842,958 | A | * | 7/1958 | Roark et al. ............... 73/38 |
| 2,889,836 | A | * | 6/1959 | Maley ............... 134/110 |
| 3,172,286 | A | * | 3/1965 | Cave et al. ............... 73/61.64 |
| 3,289,467 | A | * | 12/1966 | Parker et al. ............... 73/61.63 |
| 3,370,707 | A | * | 2/1968 | Nordstrom ............... 210/94 |
| 3,401,802 | A | * | 9/1968 | Fann ............... 210/446 |
| 3,516,478 | A | * | 6/1970 | Dunn et al. ............... 164/423 |
| 3,522,886 | A | * | 8/1970 | Clinton et al. ............... 210/345 |
| 3,702,659 | A | * | 11/1972 | Clark ............... 210/343 |
| 3,983,743 | A | * | 10/1976 | Olin et al. ............... 73/28.06 |
| 4,287,066 | A | * | 9/1981 | Greutert et al. ............... 210/464 |
| 4,375,409 | A | * | 3/1983 | Gentry ............... 210/232 |
| 4,397,177 | A | * | 8/1983 | Cain ............... 73/863.23 |
| 4,434,054 | A | * | 2/1984 | Livesey et al. ............... 210/484 |
| 4,561,289 | A | * | 12/1985 | Jones ............... 73/38 |
| 4,610,158 | A | * | 9/1986 | Lawton, Jr. ............... 73/61.64 |
| 4,637,876 | A | * | 1/1987 | Dosoudil ............... 210/331 |

(Continued)

OTHER PUBLICATIONS

International Search Report and Written Opinion, mailed Jan. 28, 2009, for PCT/US2008/073712.

(Continued)

*Primary Examiner* — John Fitzgerald

(57) ABSTRACT

The present disclosure is directed to a filter element for simulating a fracture in subterranean formations comprising a non-porous filter element configured to be disposed in a wellbore fluid testing device, the non-porous filter element having a plurality of radial perforations extending there through.

26 Claims, 5 Drawing Sheets

(56) References Cited

U.S. PATENT DOCUMENTS

| | | | |
|---|---|---|---|
| 4,640,140 A * | 2/1987 | Burghoffer et al. | 73/863.22 |
| 4,643,019 A * | 2/1987 | Jones | 73/38 |
| 4,748,849 A * | 6/1988 | Jamison et al. | 73/61.64 |
| 4,876,007 A * | 10/1989 | Naruo et al. | 210/339 |
| 4,882,055 A * | 11/1989 | Stamstad | 210/483 |
| 4,902,420 A * | 2/1990 | Pall et al. | 210/346 |
| 4,921,712 A * | 5/1990 | Malmquist | 464/77 |
| 5,100,551 A * | 3/1992 | Pall et al. | 210/346 |
| 5,292,437 A * | 3/1994 | Ford | 210/478 |
| 5,492,175 A | 2/1996 | El-Rabaa et al. | |
| 5,763,367 A | 6/1998 | Burts, Jr. | |
| 5,824,218 A * | 10/1998 | Gasser et al. | 210/337 |
| 6,269,684 B1 | 8/2001 | Maki, Jr. et al. | |
| 6,343,697 B1 * | 2/2002 | Hausdorf et al. | 210/486 |
| 6,543,276 B2 | 4/2003 | Murphy, Jr. et al. | |
| 6,685,759 B2 * | 2/2004 | Dahlin et al. | 55/465 |
| 6,710,019 B1 * | 3/2004 | Sawdon et al. | 507/136 |
| 6,971,448 B2 | 12/2005 | Slabaugh et al. | |
| 2006/0223715 A1 | 10/2006 | Svoboda et al. | |
| 2006/0254826 A1 | 11/2006 | Alberthy | |
| 2009/0291861 A1 * | 11/2009 | Sawdon | 507/110 |

OTHER PUBLICATIONS

Tehrani et al., "Designing Fluids for Wellbore Strengthening-Is It an Art?" In: 2007 AADE National Technical Conference and Exhibition, AADE-07-NTCE-75.

* cited by examiner

METHOD AND APPARATUS FOR FLUID LOSS MEASUREMENTS OF WELLBORE FLUIDS

BACKGROUND

1. Field of the Disclosure

The present disclosure generally relates to apparatus and methods for testing wellbore fluids used in subterranean operations. More specifically, the present disclosure relates to apparatus and methods for simulating wellbore fractures and testing wellbore fluids containing loss circulation materials using a testing device comprising a filter element with radial perforations extending there through.

2. Background Art

When drilling or completing wells in earth formations, various fluids typically are used in the well for a variety of reasons. The fluid often is generally either oil-based or water-based. For the purposes herein, such fluid will be referred to as "well fluid." Common uses for well fluids include: lubrication and cooling of drill bit cutting surfaces while drilling generally or drilling-in (i.e., drilling in a targeted petroliferous formation), transportation of "cuttings" (pieces of formation dislodged by the cutting action of the teeth on a drill bit) to the surface, controlling formation fluid pressure to prevent blowouts, maintaining well stability, suspending solids in the well, minimizing fluid loss into and stabilizing the formation through which the well is being drilled, minimizing fluid loss into the formation after the well has been drilled and during completion operations such as, for example, perforating the well, replacing a tool, attaching a screen to the end of the production tubulars, gravel-packing the well, or fracturing the formation in the vicinity of the well, displacing the fluid within the well with another fluid, cleaning the well, testing the well, fluid used for emplacing a packer, abandoning the well or preparing the well for abandonment, and otherwise treating the well or the formation.

Lost circulation is a recurring drilling problem, characterized by loss of drilling mud into downhole formations that are fractured, highly permeable, porous, cavernous, or vugular. These earth formations can include shale, sands, gravel, shell beds, reef deposits, limestone, dolomite, and chalk, among others. Other problems encountered while drilling and producing oil and gas include stuck pipe, hole collapse, loss of well control, and loss of or decreased production.

Induced mud losses may also occur when the mud weight, required for well control and to maintain a stable wellbore, exceeds the fracture resistance of the formations. A particularly challenging situation arises in depleted reservoirs, in which the drop in pore pressure weakens hydrocarbon-bearing rocks, but neighboring or inter-bedded low permeability rocks, such as shales, maintain their pore pressure. This can make the drilling of certain depleted zones impossible because the mud weight required to support the shale exceeds the fracture resistance of the sands and silts.

Other situations arise in which isolation of certain zones within a formation may be beneficial. For example, one method to increase the production of a well is to perforate the well in a number of different locations, either in the same hydrocarbon bearing zone or in different hydrocarbon bearing zones, and thereby increase the flow of hydrocarbons into the well. The problem associated with producing from a well in this manner relates to the control of the flow of fluids from the well and to the management of the reservoir. For example, in a well producing from a number of separate zones (or from laterals in a multilateral well) in which one zone has a higher pressure than another zone, the higher pressure zone may disembogue into the lower pressure zone rather than to the surface. Similarly, in a horizontal well that extends through a single zone, perforations near the "heel" of the well, i.e., nearer the surface, may begin to produce water before those perforations near the "toe" of the well. The production of water near the heel reduces the overall production from the well.

In attempting to cure these and other problems, loss control materials (LCM) have been employed. Historically, LCM's have been proposed to address the fractures and joints within the wellbore, however the LCM's are frequently tested for efficacy during actual field trials. What is still needed is a device that allows for the evaluation of LCM's in a laboratory setting. Accordingly, there exists a continuing need for a wellbore test cell and method that simulates currently recognized field tests.

SUMMARY OF THE DISCLOSURE

One aspect of the present invention is a filter element for simulating a fracture in rock formation, the filter element comprising a non-porous filter medium configured to be disposed in a wellbore fluid testing device, the non-porous filter medium having a plurality of radial perforations extending there through. The radial perforations comprise a perforation width less than the width of the outlet of the wellbore fluid testing device, and preferably a perforation width that ranges from about 10 microns to about 2000 microns. The filter element comprises a reusable plate made of a material such as perforated ceramic plates, polycarbonate plates, metallic plates, and combinations thereof. The filter element further comprises a plurality of feet.

Another aspect of the present invention is method of evaluating the performance of a wellbore fluid, wherein the wellbore fluid comprises a base fluid and a loss circulation material, wherein the method comprises passing the wellbore fluid through a non-porous filter medium, the non-porous filter medium having a plurality of radial perforations extending there through. The radial perforations comprise a perforation width less than the width of the outlet of the wellbore fluid testing device, and preferably a perforation width that ranges from about 10 microns to about 2000 microns. The filter element comprises a reusable plate made of a material such as perforated ceramic plates, polycarbonate plates, metallic plates, and combinations thereof. The filter element further comprises a plurality of feet.

DETAILED DESCRIPTION

Generally, embodiments disclosed herein relate to apparatus and methods for testing wellbore fluids used in subterranean operations. More specifically, embodiments disclosed herein relate to apparatus and methods for testing wellbore fluids containing loss circulation materials used in subterranean operations. More specifically still, embodiments disclosed herein relate to apparatus and methods for testing wellbore fluids containing loss circulation materials using a filter element resistant to bowing, which may be disposed in and sealingly engaged within a wellbore fluid testing device.

Embodiments of the present disclosed may provide for the testing of well bore fluids containing loss circulation materials typically tested using the devices discussed above. Those of ordinary skill in the art will appreciate that the device and methods disclosed herein may be used to test both oil-based and water-based wellbore fluids containing varied loss circulation materials, such as, carbonates, fibers, nutshells, wood, dust, and other materials known in the art.

Figure 1:
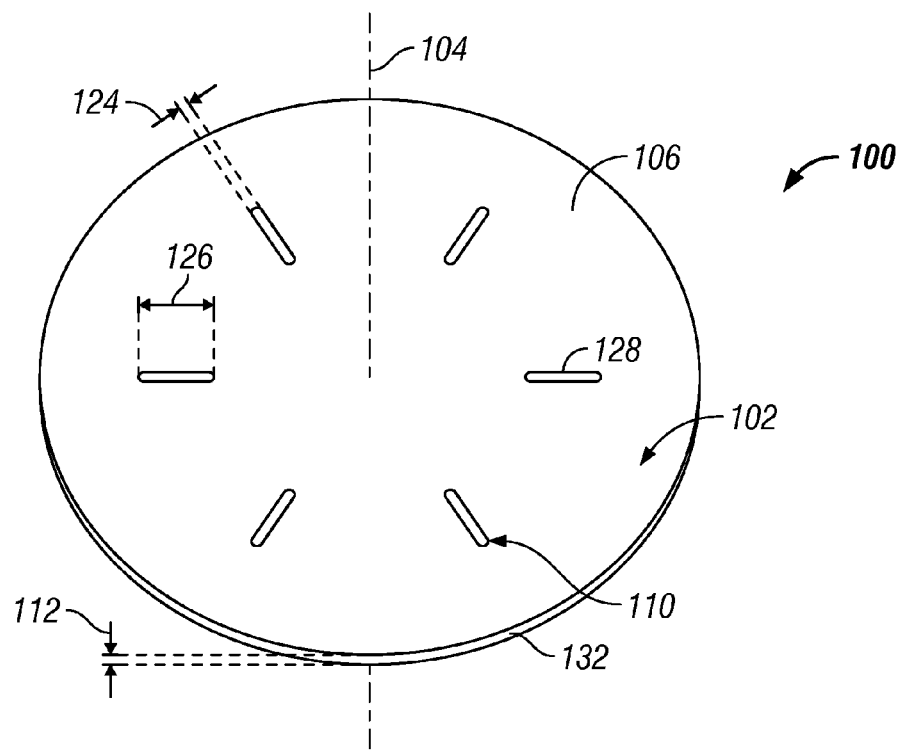
FIG. 1 shows a top view of a filter element according to embodiments of the present disclosure.
Figure 8:
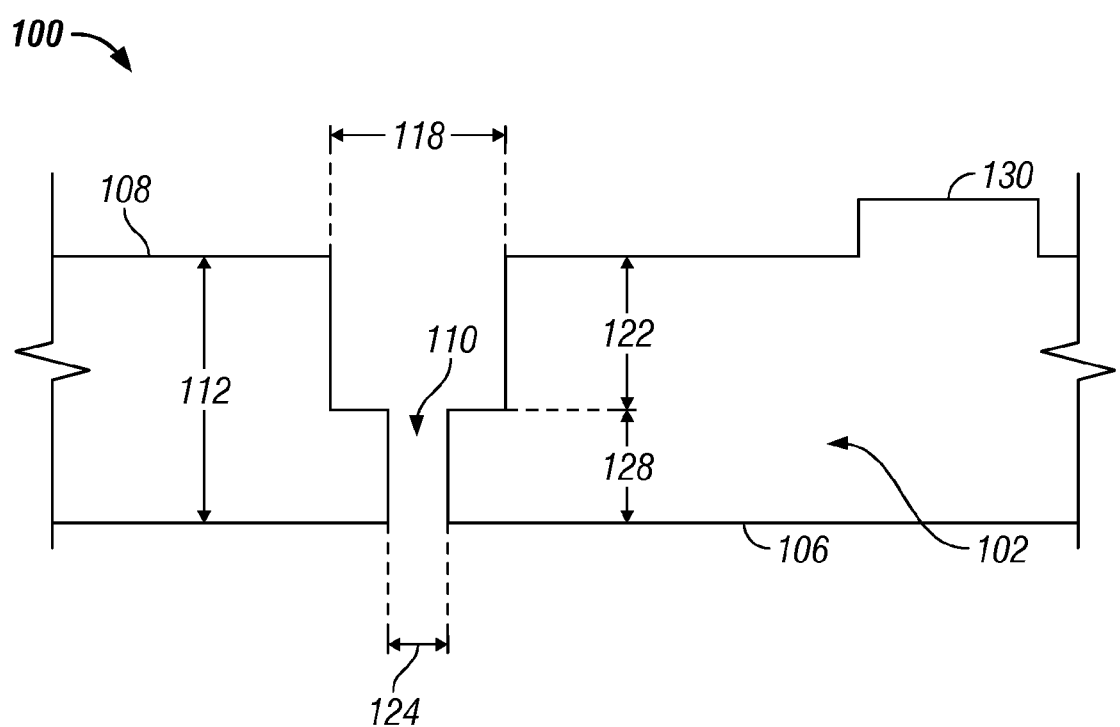
FIG. 8 shows a partial section diagram of a filter element of the present disclosure.

Referring to FIGS. 1 and 8, those of ordinary skill in the art will appreciate that the filter element 100 may generally include a plate 102, preferably of a non-porous, rigid material comprising a plurality of perforations 110 disposed through plate 102. Filter element 100 may be formed of any type of material used to test wellbore fluids, including perforated ceramic, polycarbonate, metallic plates, or combinations thereof. In an embodiment, plate 102 may comprise metals such as stainless steel, such as grade 303, 310, 316 stainless steel, and combinations thereof; carbon steel; titanium, non-porous ceramic, carbon fibers, and combinations thereof. Those of ordinary skill in the art will appreciate that filter element 100 may also be formed from other materials capable of withstanding the pressures and temperatures used in wellbore fluid tests. For example, test devices currently utilized for testing wellbore fluids may introduce pressures as high as 2500 psi. Thus, it may be desirable for filter element 100 to be capable of withstanding similar pressures.

Figure 2:
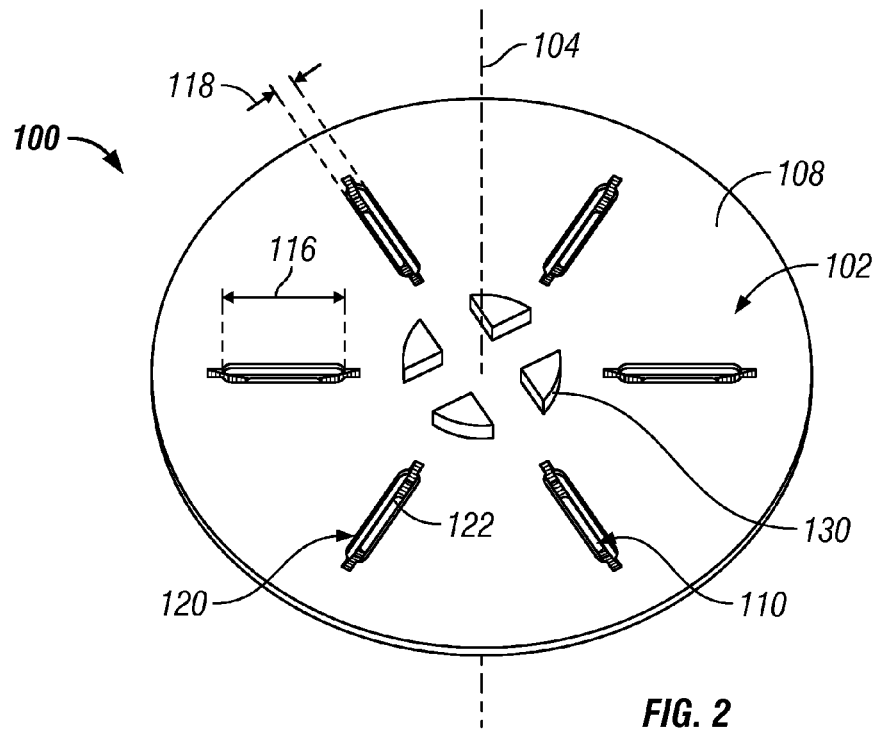
FIG. 2 shows a bottom view of a filter element according to embodiments of the present disclosure.

In an embodiment, a filter element 100 for simulating a fracture in rock formation comprises a plate 102 dimensioned to sealingly engage an inner surface of a wellbore fluid testing device, such that filter element 100 separates an inlet of the testing device from an outlet of the testing device. Plate 102 may comprise a central axis 104 located perpendicular to a top face 106, wherein the top face is separated from a bottom face 108 (see FIG. 2) along central 104 axis by a plate thickness 112. As shown in FIG. 2, in an embodiment, plate 102 may comprise a plurality of indentations, also referred to as valleys, furrows, and the like, into which the plurality of perforations 110 are arranged. The plurality of furrows 120 may be disposed on the top face 106, bottom, face 108, or a combination thereof. In an embodiment, plate 102 includes a plurality of furrows 120 disposed partially through the plate, wherein each of the furrows 120 has a furrow length 116, a furrow width 118, and a furrow depth 122, wherein each of the plurality of furrows 120 protrudes into plate 102 by furrow depth 122, and wherein furrow depth 122 is less then plate thickness 112. Plate 102 may further comprise a plurality of perforations 110 disposed through plate 102, wherein each perforation 110 has a perforation width 124, a perforation length 126, and a perforation thickness 128. Each one of the plurality of perforations 110 is preferably disposed concentrically within one each of the plurality of furrows 120 such that perforation thickness 128 of each perforation 110 is equal to the difference between plate thickness 112 and furrow depth 122.

In an embodiment, filter element 100 has a plurality of perforations 110 extending there through, radially disposed about central axis 104. As shown FIGS. 1 and 2, the plurality of perforations 110 have perforation length 126 oriented along a line or ray extending from central axis 104 to an outer edge 132 of plate 102. As such, the perforations 110 are arranged in a hub and spoke pattern, preferably equidistant from one another. It is believed that this radial configuration of perforations 110 evenly distributes stress across plate 102 of filter element 100, thereby reducing bowing of filter element 100 upon application of pressure during testing. Further, it is believed that the radial configuration diffuses the pressures across the test zone of the wellbore test device. Those of ordinary skill in the art will appreciate that other configurations of perforations 110 are possible, as long as the configuration results in a diffusion of pressure across the test zone and an essentially equal distribution of stress across filter element 100 upon application of pressure.

Figure 3:
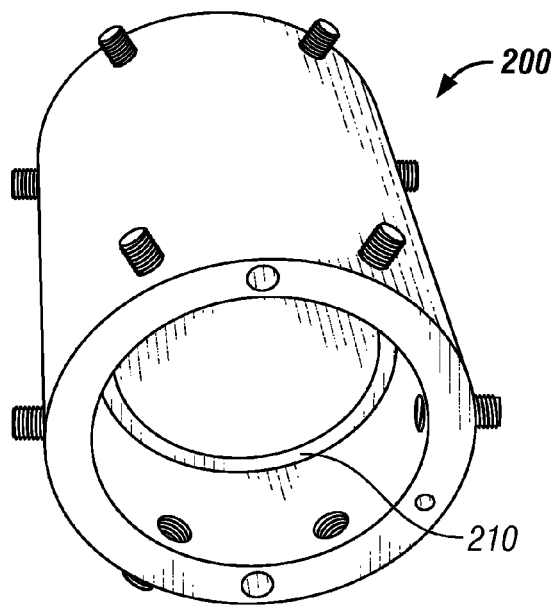
FIG. 3 shows an end view of a cell body of a wellbore fluid test device according to embodiments of the present disclosure.

In an embodiment, filter element 100 may include more than one perforation 110, preferably at least 3 perforations 110, more preferably at least 6 perforations 110, as shown in FIGS. 1 and 3, which depicts six perforations 110 in filter element 100. Any number of perforations 110 is possible, and is preferably arranged in a hub and spoke radial configuration. One of ordinary skill in the art will appreciate that the number of perforations 110 is dependent upon the total percent of open space desired in filter element 100. Accordingly, as a larger percent of open space is desired, the total number of perforations 110 will increase.

Figure 5:
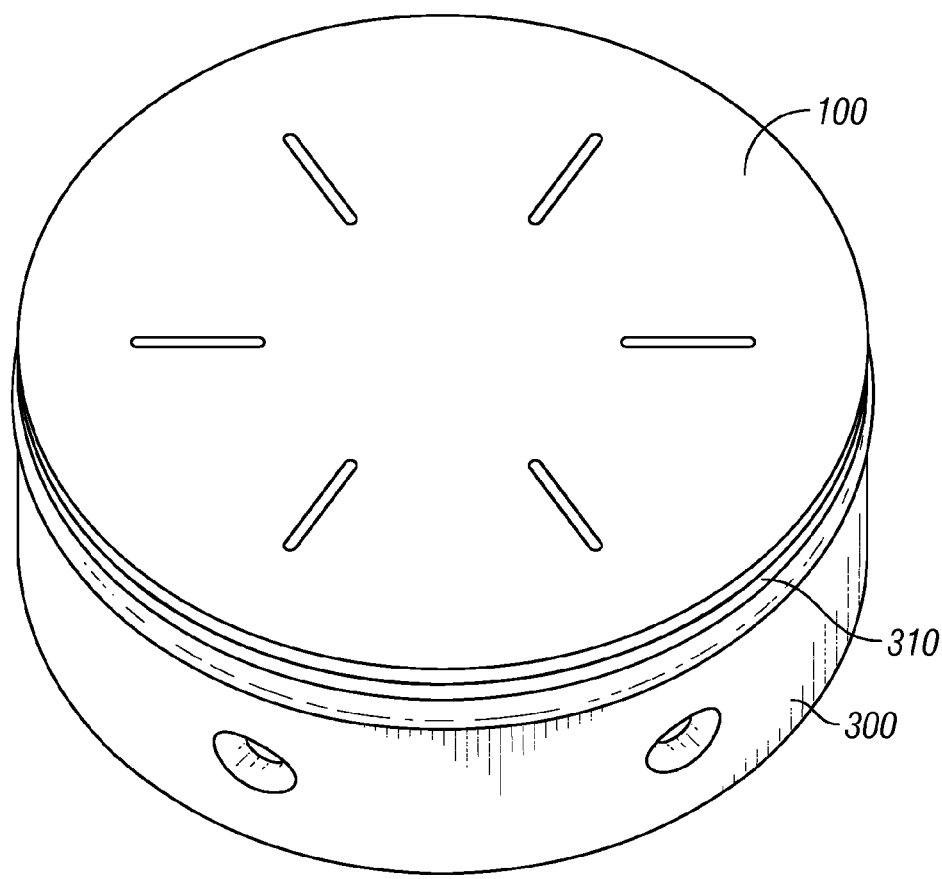
FIG. 5 shows a top view of a positioned filter element and end plate of a wellbore fluid test device according to embodiments of the present disclosure.

Perforations 110 are dimensioned within filter element 100 to simulate fractures or joints in a wellbore. Perforation width 124 may be varied to provide a mechanism for simulating conditions, including the degree of fracture and/or joint present in a particular wellbore. Referring to FIGS. 1 and 5, perforations have perforation widths 124 sized smaller than the width of outlet 320. This sizing prevents clogging outlet 320 with loss circulation materials. In some embodiments, perforations 110 may have a perforation width 124 in the range of about 100 microns to about 3000 microns. In other embodiments, perforations 110 have perforation widths 124 in the range of about 200 microns to about 2000 microns. In yet other embodiments, perforations 110 have perforation widths 124 in the range of about 500 microns to about 1000 microns. While FIGS. 1 and 2 depict perforations 110 having apparent equally sized perforation widths 124, one of ordinary skill in the art will appreciate that the perforation widths 124 may vary in size. In other words, if filter element 100 has six perforations 110, it may be advantageous to provide a different perforation width 124 for each perforation 1.10 extending there through. For example, a single filter element 100 may have the following perforation widths 124: 100 micron, 200 micron, 500 micron, 1000 micron, 2000 micron, and 3000 micron. Varying the perforation widths 124 of each perforation 100 permits performing one test to evaluate a loss circulation material over multiple degrees of fracture and/or joint. Further, this variance provides a means of quality control of loss circulation materials.

Each perforation 110 is preferably disposed within a corresponding furrow 120. Furrows 120 simulate the surface effect of the fracture. Additionally, disposing perforation 110 within a corresponding furrow 120 allows for an accurate cutting of the perforation into the plate 102, and also allows for control of perforation thickness 128. One of ordinary skill of the art may appreciate that furrow length 116 depends upon the material chosen for filter element 100. In an embodiment, furrow length 116 is sized larger than perforation 110, thereby permitting perforation 110 to be disposed within the corresponding furrow 120. In some embodiments, perforation 110 is concentrically disposed within the corresponding furrow 120.

Figure 4:
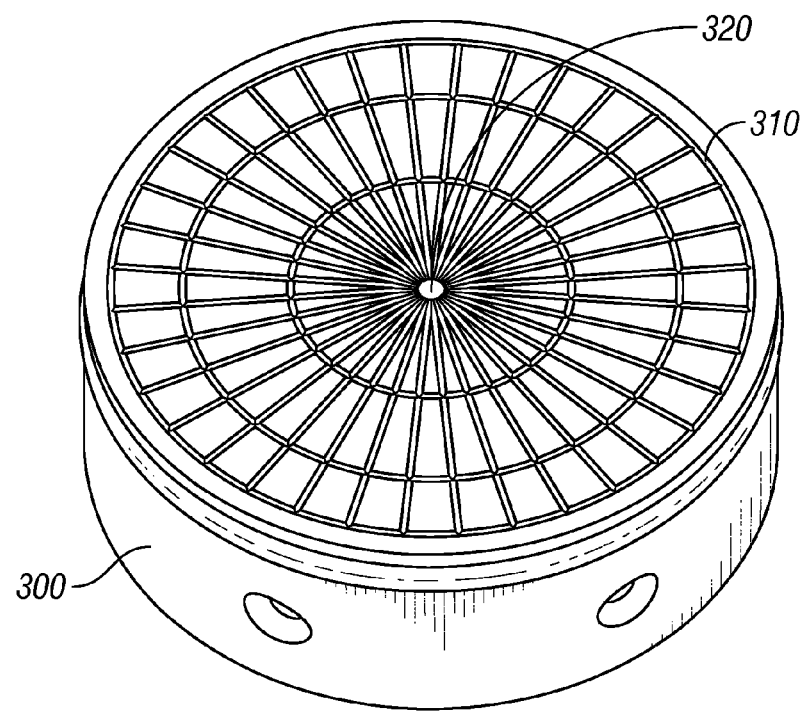
FIG. 4 shows a top view of an end plate of a wellbore fluid test device according to embodiments of the present disclosure.
Figure 6:
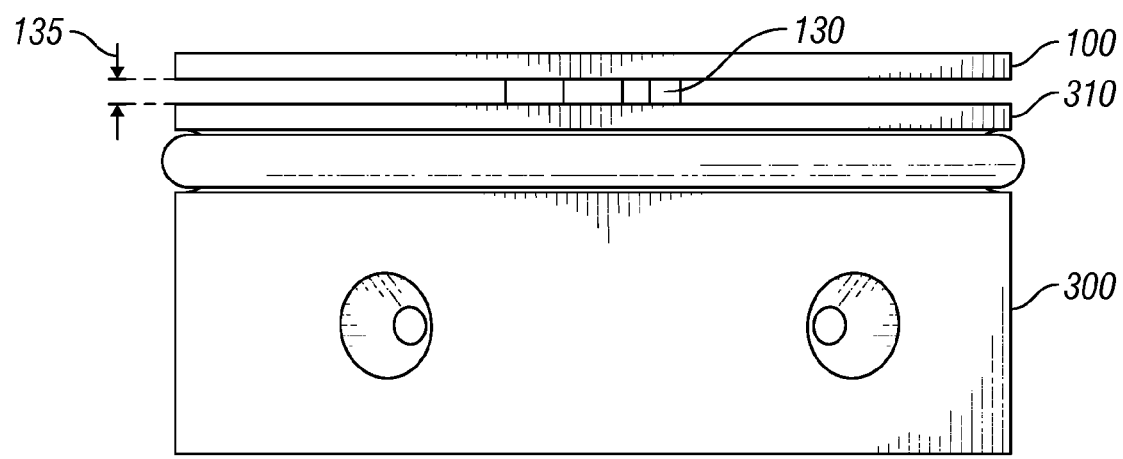
FIG. 6 shows a side view of a positioned filter element and end plate of a wellbore fluid test device according to the embodiments of the present disclosure.

Referring to FIGS. 2, 4, and 6, filter element 100 may further comprise a plurality of spacers, also referred to as feet 130 for supporting filter element 100 and providing a space below filter element 100 such that filtrate may be discharged through an outlet 320 of a testing device (see FIG. 4.) Accordingly, filter element 100 may further comprise a plurality of feet 130 attached to, and depending away from bottom face 108, wherein the plurality of feet 130 are dimensioned and arranged on bottom face 108 to provide support for filter element 100 during testing to evaluate the performance of a wellbore fluid. In an embodiment, the plurality of feet 130 have a feet height 135 (See FIG. 5) dimensioned to contact a surface within the testing device such that perforation width 124 of the plurality of perforations 110 is not substantially enlarged due to flexing of the plate 102 upon application of pressure across filter element 100 during testing.

Feet 130 have a feet height 135 sufficient enough to create a clearance for the passage of filtrate to outlet 320. In some embodiments, feet height 135 is in the range of about 10 microns to about 10,000 microns. However, one of ordinary skill in the art will appreciate that any feet height 135 is possible as long as filtrate is allowed to pass to outlet 320.

In an embodiment, the plurality of feet 130 may be disposed between central axis 104 and the plurality of furrows 120, between each of the furrows 120, between each of furrows 120 and outer edge 132, or a combination thereof.

As illustrated in FIG. 2, feet 130 may be radially configured about central axis 104, and equally spaced with respect to each other. Feet 130 are also preferably configured on the same side of filter element 100, proximate the central point of filter element 100. One of ordinary skill in the art will appreciate that the number of feet utilized will depend upon the size of the feet, as well as the feet 130 position on filter element 100. In some embodiments, there are at least two feet 130 disposed on filter element 100. In other embodiments, there are at least four feet 130 disposed on filter element 100.

The instant filter element 100 may be used in evaluating the performance of a wellbore fluid. In an embodiment, a method of evaluating the performance of a wellbore fluid, wherein the wellbore fluid comprises a base fluid and a loss circulation material, may comprise the steps of passing at least a portion of the wellbore fluid through a filter element and measuring the amount of fluid which pass through the filter element. Measuring the amount of filtrate that passes through filter element 100 permits the evaluation of fluid loss.

In an embodiment, filter element 100 may be used in a method of evaluating the performance of a wellbore fluid, wherein the wellbore fluid comprises a base fluid and a loss circulation material, wherein the method comprises the steps of:

1) engaging a filter element within a wellbore testing device, such that the filter element is sealingly engaged between an inlet of the testing device and an outlet of the testing device;
2) charging the testing device with a portion of the wellbore fluid; and
3) measuring the amount of fluid which passes through the filter element.

Filter element 100 may be used in conjunction with various wellbore fluid test devices, such as Pore Pressure Transmission (PPT), Production Screen Tester (PST), and double-ended High Temperature, High Pressure (HTHP) test devices.

Rerring to FIGS. 3 and 4, components of a HTHP test cell are depicted. The HTHP test cell may include a cell body 200 and a bottom end plate 300 having a bottom end plate face 310. As one of ordinary skill in the art will appreciate, filter element 100 may be disposed within similar and/or other wellbore test devices, such as product screen testers, permeability plugging apparatus testers, and the like. In use, the instant filter element 100 is sealingly engaged within an inner surface of a wellbore fluid testing device such that the plurality of perforations 110 provides fluid communication between an inlet and an outlet of the testing device.

In the embodiments shown in FIGS. 3-6, filter element 100 is disposed within cell body 200 such that top face 106 engages a lip 210 within cell body 200. One or more additional components e.g., screens, spacers, and the like, and/or sealing members e.g., o-rings, gaskets, and the like, may also be disposed between lip 210 and top face 106 of filter element 100. A bottom end plate 300 may also be inserted into cell body 200 and securably attached to cell body 200. End plate 300 may be attached to cell body 200 using, for example, screws, rivets, or other mechanical fasteners, as is common in the art. In other aspects, one or more of end plates 300 may be removably attached to cell body 200 using hinges, retainer bars, threaded members, and/or other means of removably attaching components, as is known in the art. Those of ordinary skill in the art will appreciate that the specific type of attachment is not a limitation on the scope of the present disclosure. However, embodiments disclosed herein may include attachment of bottom end plate 300 to cell body 200 such that a sealing engagement is formed. As such, drilling fluids injected into cell body 200 may only be discharged from the system through specified outlets. To prevent the discharge of drilling fluids through interface associated with bottom endplate 300, cell body 200, and other surfaces, a plurality of seals may be disposed between the various components. The seals may be formed from, for example, rubbers and/or elastomers. Those of ordinary skill in the art will appreciate that in alternate embodiments, cell body 200 may be formed such that only one end plate, for example either a top end plate or a bottom end plate 300, is required. In such an embodiment, the one end plate may be securably attached to the cell body 200, according to the methods described above. Filter element 100 may be disposed inside an inner chamber of cell body 200. In this embodiment, filter element 100 may be disposed substantially perpendicular to a central axis of cell body 200.

Test wellbore fluid may be injected into cell body 200 via a fluid inlet (not shown). Fluid inlet may be located proximate a top end cap (not shown), substantially closer to the top end cap than filter element 100. As such, a volume of drilling fluid injected into cell body 200 may not be limited by the placement of the fluid inlet. However, in alternate embodiments, it may be beneficial for the fluid inlet to be disposed in closer proximity to filter element 100, and as such, the precise location of the fluid inlet is not meant as a limitation on the scope of the present disclosure. Generally, the fluid inlet is configured to provide the test wellbore fluid to cell body 200, and as such, the fluid inlet may be in fluid communication with a drilling fluid storage reservoir (not shown) and a plurality of valves (not shown) for controlling the flow of the drilling fluid there through.

Referring to FIGS. 3-6, embodiments of cell body 200 also include a filtrate outlet 320 configured to receive a discharge flow of filtrate from cell body 200. To maintain pressure and fluid flow through the wellbore test device, it is desirable to avoid plugging filtrate outlet 320. As previously discussed, filter element 100 has a plurality of radially configured perforations extending there through. Accordingly, in some embodiments, perforation width 124 is less than the width of filtrate outlet 320 of the wellbore fluid testing device.

Generally, filtrate outlet 320 may be disposed as a conduit through bottom end plate 300, thereby providing fluid communication between cell body 200 and downstream processing and/or collection components. In this embodiment, filtrate outlet 320 is located below filter element 100 such that as filtrate passes through filter element 100, the filtrate may be discharged from cell body 200. Filtrate outlet 320 may be disposed below filter element 100 along any portion of cell body 200 or bottom end plate, so as to receive a flow of filtrate passing there through. Thus, in certain aspects, filtrate outlet 320 may be disposed as a conduit through bottom end plate 300, cell body 200, or through other components of the wellbore fluid test device.

Cell body 200 may also include a pressurization inlet (not shown) configured to allow for the pressurization of cell body 200. The pressurization inlet may be disposed anywhere on cell body 200 such that a supply of air (e.g., oxygen-free nitrogen and other inert gases) may be pumped into cell body 200 to provide a positive pressure to a fluid contained therein. The pressurization inlet may be disposed as a conduit through the top end plate, and may be in fluid communication with an air compression device (not shown) capable of providing a pressurization gas to cell body 200. In certain embodiments, the pressurization inlet may be in fluid communication with additional components such as, for example, remote-controlled pressure regulator valves (not shown) that may be used to adjust the pressure of a gas. Exemplary pressures may include providing a pressure between 10 psi and 3000 psi. Additional components may include pressure gauges (not shown), relief valves (not shown), and other components used during pressurization of testing cells known to those of ordinary skill in the art.

In certain embodiments, a heating jacket may be disposed around cell body 200 and/or top end plate and bottom end plate 300. Heating jacket may include a heating element (not shown) disposed or formed integral to the heating jacket. The heating element may be configured to a control system (not shown) such that a temperature level of the heating jacket may be controlled. The temperature of the heating jacket may be determined via a thermocouple (not shown) disposed in the heating jacket. Additionally, the heating jacket may include a plurality of slits/conduits to accommodate components of the cell body 200. For example, the slits/conduits in the heating jacket may accommodate any of the inlets and/or outlets described above.

Figure 7:
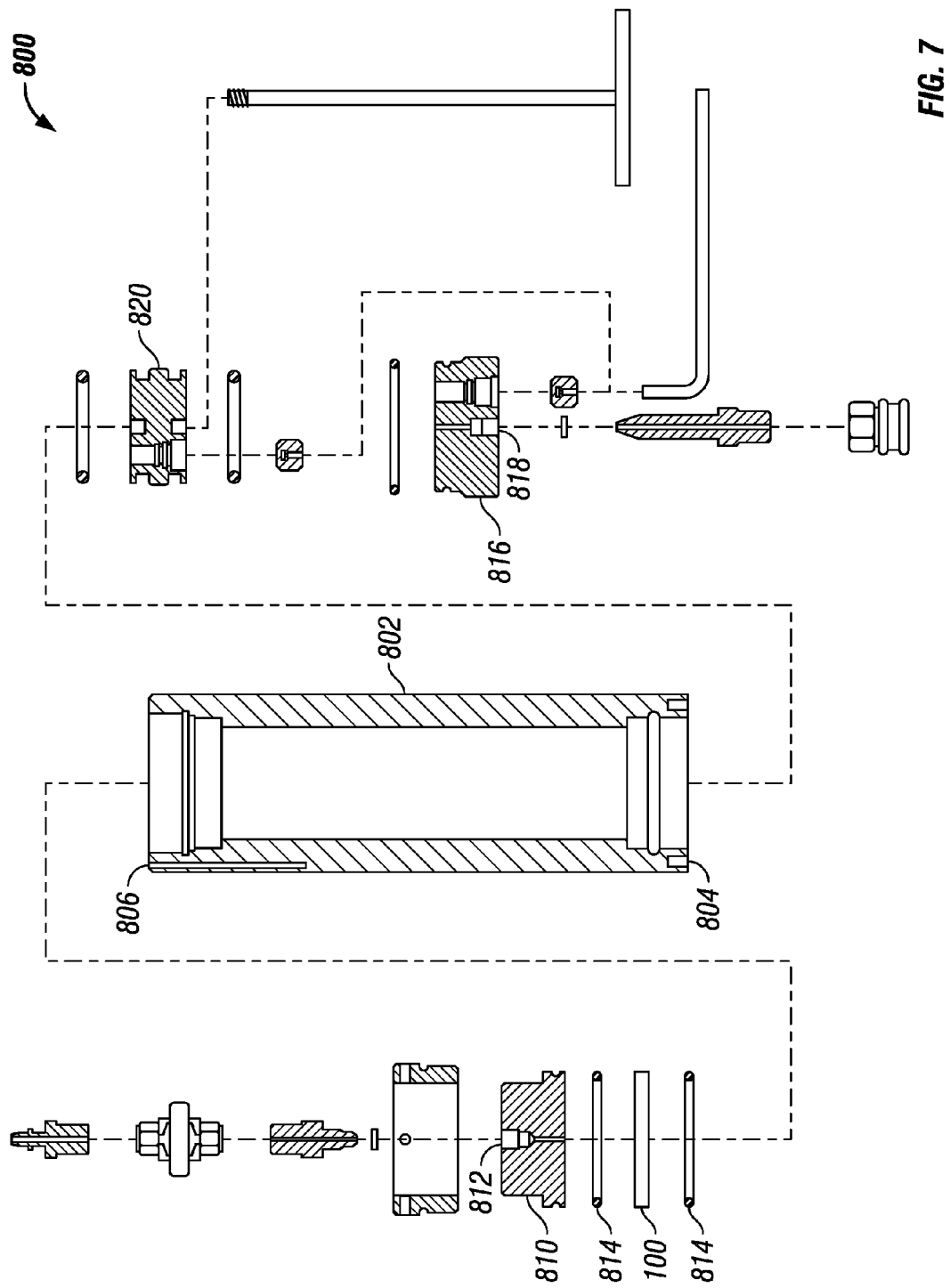
FIG. 7 shows an exploded section diagram of a wellbore testing device.

Another example of a wellbore fluid test device is shown in FIG. 7, in which a permeability plugging apparatus testing device is shown as an exploded view of the components. In general, a suitable testing device 800 may include a cell body 802, having a cell inlet end 804 and a cell outlet end 806. Filter element 100 may be sealingly engaged between cell outlet end 806 and a cell outlet adapter 810, which comprises an outlet 812 of testing device 800. Filter element 100 may be sealingly engaged with an inner surface of cell body 802 utilizing one or more o-rings 814, and/or other suitable means of providing a seal when outlet adapter 810 is engaged with cell outlet end 806. Testing device 800 may further include an inlet adapter 816, which may include an inlet 818 of testing device 800. In the embodiment shown in FIG. 7, testing device 800 includes a piston 820 which is capable of moving within cell body 802 and which may be actuated via a hydraulic pump (not shown) connected to inlet 818 to produce pressure on a fluid contained within cell body 802 between piston 820 and filter element 100. Backpressure may also be applied to cell outlet 812 during testing.

Those of ordinary skill in the art will appreciate that specific components of wellbore fluid test device may not be necessary, and as such, the scope of the present disclosure should only be limited by the appended claims.

A method to evaluate the performance of a wellbore fluid, wherein the wellbore fluid comprises a base fluid and a loss circulation fluid, initially the test fluid may be injected and/or otherwise disposed within the wellbore fluid test device, e.g., via a test fluid injection pump (not shown). The test fluid may have been previously stored in a storage vessel (not shown) in fluid communication with the injection pump.

Once a known volume of test fluid is injected into the wellbore fluid test device, the internal chamber of the wellbore fluid test device is pressurized. A pressure regulator valve may be used to adjust the gas pressure, such that a preferable pressure range is achieved. Those of ordinary skill in the art will appreciate that in certain embodiments, it may be preferable to test the drilling fluid in an environment between 50 psi and 2500 psi, however, in alternate embodiments, the pressure may range between 100 and 500 psi. The pressure may be measured by a pressure gauge, while a relief valve may, be included to prevent an incidental pressure build-up. A valve may be used to regulate the injection of gas to the pressurization inlet.

During operation of the wellbore, fluid test device, the wellbore fluid separates into a filtrate and a residual fluid, as perforations 110 of filter element 100 become plugged with loss circulation materials. Filtrate that passes through filter element 100 may exit the wellbore fluid test device via filtrate outlet, and collected in a filtrate collection vessel in one embodiment, the filtrate collection vessel may include a graduated cylinder having two different cross-sectional areas, thereby allowing for the collection and measuring of the filtrate.

After the testing phase, the loss circulation materials that formed on filter element 100 during the testing may be examined. Generally, after the testing phase is complete, the wellbore fluid test device is allowed to cool and is de-pressurized by gradually opening the valve to allow gas in the internal chamber of cell body to exit via a vent. The test fluid may then be discharged from the wellbore fluid test device via a valve connected to a vacuum pump. Thus, residual wellbore fluid may be vacuumed from the wellbore fluid test device and discarded and/or recycled accordingly.

The loss circulation materials may be examined and the mechanism by which the loss circulation material blocked the perforations 110 may be determined. Table 1 details the results when different types of loss circulation materials were tested to evaluate the effectiveness at bridging perforations 110. In the evaluations, the spurt amount represents the amount of material which passes through the particular filter element prior to cessation of filtrate flow. A value of "T" indicates a failure of the LCM material to plug the perforations of the filter element.

TABLE 1

| | Test Material | Test Matrix | | | | | |
|---|---|---|---|---|---|---|---|
| | Fibers, Nutshells-Fine. | Addition (ppb) | | | Spurt (ml) | | |
| 250 micron perforations | Fibers, nutshells-Fine. | 5 | 10 | 20 | 3 | 1 | 0 |

TABLE 1-continued

| Test Material | | Test Matrix | | | | | |
|---|---|---|---|---|---|---|---|
| 500 micron perforations | Fibers, nutshells-Fine. | 5 | 10 | 20 | T | T | T |
| 750 micron perforations | Fibers, nutshells-Fine. | 5 | 10 | 20 | T | T | T |
| 1000 micron perforations | Fibers, nutshells-Fine. | 5 | 10 | 20 | T | T | T |
| | Fibers nutshells-Coarse. | Addition (ppb) | | | Spurt (ml) | | |
| 250 micron perforations | Fibers, nutshells-Coarse. | 5 | 10 | 20 | 0 | 0 | 0 |
| 500 micron perforations | Fibers, nutshells-Coarse. | 5 | 10 | 20 | 6 | 2 | 0 |
| 750 micron perforations | Fibers, nutshells-Coarse. | 5 | 10 | 20 | 17 | 8 | 0 |
| 1000 micron perforations | Fibers, nutshells-Coarse. | 5 | 10 | 20 | T | T | 0 |
| | 250 μm sized carbonite. | Addition (ppb) | | | Spurt (ml) | | |
| 250 micron perforations | 250 μm sized carbonite. | 5 | 10 | 20 | 0 | 0 | 0 |
| 500 micron perforations | 250 μm sized carbonite. | 5 | 10 | 20 | T | T | T |
| 750 micron perforations | 250 μm sized carbonite. | 5 | 10 | 20 | T | T | T |
| 1000 micron perforations | 250 μm sized carbonite. | 5 | 10 | 20 | T | T | T |
| | Wood, dust, fibers-Fine. | Addition (ppb) | | | Spurt (ml) | | |
| 250 micron perforations | Wood, dust, fibers-Fine. | 5 | 10 | 20 | 1 | 0 | 0 |
| 500 micron perforations | Wood, dust, fibers-Fine. | 5 | 10 | 20 | 9 | 2 | 0 |
| 750 micron perforations | Wood, dust, fibers-Fine. | 5 | 10 | 20 | T | 11 | 1 |
| 1000 micron perforations | Wood, dust, fibers-Fine. | 5 | 10 | 20 | T | T | T |

Advantageously, embodiments of the present disclosure may provide for a testing device fix testing wellbore fluids and loss circulation materials. As such, the wellbore fluid test device may be able to implement a testing phase and an analysis phase, and determine properties of wellbore fluids and loss circulation materials. Because of the configuration of perforations 110 and feet 130, filter element 100 resists bowing, and an accurate performance of loss circulation materials may be determined.

Embodiments of the present disclosure may also provide for the effectiveness of specific loss circulation materials to be analyzed. Because the wellbore fluid test device simulates wellbore fractures and joints, evaluation of loss circulation materials in the laboratory environment is possible. Such evaluations may result in more efficient use of loss circulation materials in wellbore operations, thereby decreasing the costs associated with evaluating fluid performance during the wellbore operations.

While the present disclosure has been described with respect to a limited number of embodiments, those skilled in the art, having benefit of this disclosure, will appreciate that other embodiments may be devised which do not depart from the scope of the present disclosure described herein. Accordingly, the scope of the present disclosure should be limited only by the attached claims.

What is claimed is:

1. A method comprising:
    obtaining a known volume of wellbore fluid comprising a base fluid and loss circulation materials;
    passing the wellbore fluid through a simulated wellbore fractures thereby plugging the simulated wellbore fractures with the loss circulation materials; and
    measuring the amount of filtrate generated from passing the wellbore fluid through the simulated wellbore fracture;
    wherein the simulated wellbore fracture comprises a plurality of perforations each disposed within a furrow and located radially about a central axis of the simulated wellbore fracture and extending through a non-porous material that forms a plate, the furrow having a depth less than the plate thickness, the plurality of perforations each having a perforation length oriented along a line extending from the central axis to an outer edge of the simulated wellbore fracture.

2. The method of claim 1, wherein the plurality of perforations comprises perforation width ranges from about 10 microns to about 2000 microns.

3. The method of claim 1, wherein the non-porous material comprises a material selected from the group consisting of perforated ceramic plates, polycarbonate plates, metallic plates, and combinations thereof.

4. The method of claim 1, wherein the plurality of perforations are equally spaced with respect to each other.

5. The method of claim 1, wherein the non-porous material further comprises a plurality of feet equally spaced with respect to each other.

6. A method comprising:
    obtaining a known volume of wellbore fluid comprising a base fluid and loss circulation materials;
    injecting the wellbore fluid into an inlet of a testing device;
    passing the wellbore fluid through a simulated wellbore fracture comprising a plurality of perforations each disposed within a furrow and located radially about a central axis of the simulated wellbore fracture and extending through a non-porous material forming a plate, the furrow having a depth less than the plate thickness, the plate sealingly engaged between the inlet of the testing device and an outlet of the testing device, the plurality of perforations each having a perforation length oriented along a line extending from the central axis to an outer edge of the simulated wellbore fracture;
    measuring the amount of filtrate generated from passing the wellbore fluid through the simulated wellbore fracture; and
    wherein the simulated wellbore fracture becomes plugged with loss circulation materials from the wellbore fluid.

7. The method of claim 6, further comprising pressurizing the testing device.

8. The method of claim 6, further comprising heating the testing device.

9. The method of claim 6, wherein the testing device is selected from the group consisting of: a pore pressure transmission device, a double-ended high-temperature high pressure test cell, and a production screen testing device.

10. The method of claim 6, wherein the non-porous material comprises a material selected from the group consisting of perforated ceramic plates, polycarbonate plates, metallic plates, and combinations thereof.

11. The method of claim 6, wherein the plurality of perforations comprises perforation width ranges from about 10 microns to about 2000 microns.

12. The method of claim 6, wherein the plurality of perforations are equally spaced with respect to each other.

13. The method of claim 6, wherein the non-porous material further comprises a plurality of feet equally spaced with respect to each other.

14. A wellbore fluid testing apparatus comprising:
a filter non-porous plate forming a having a plurality of perforations extending there through, the plurality of perforations each disposed within a furrow and located radially about a central axis of the filter, the furrow having a depth less than the plate thickness, the plurality of perforations each having a perforation length oriented along a line extending from the central axis to an outer edge of the filter,
wherein the plurality of perforations simulate fractures in a wellbore.

15. The apparatus of claim 14, wherein the plurality of perforations receive a wellbore fluid allowing the passing of a filtrate, the plurality of perforations plugged by loss circulation materials in the wellbore fluid.

16. The apparatus of claim 14, wherein the filter element further comprises:
a plurality of spacers depending away from a bottom face of the filter element.

17. The apparatus of claim 14, wherein the non-porous material comprises material selected from the group consisting of perforated ceramic plates, polycarbonate plates, metallic plates, and combinations thereof.

18. The apparatus of claim 14 further comprising:
a cell body disposed within the wellbore fluid testing apparatus, the cell body with a lip to engage the filter element.

19. The apparatus of claim 18, further comprising:
a pressurization inlet to allow for pressurization of the cell body.

20. The apparatus of claim 19, further comprising:
an air compression device in communication with the pressurization inlet to provide a pressurization gas to the cell body.

21. A method comprising:
passing a wellbore fluid with loss circulation materials through a wellbore fluid testing apparatus comprising a non-porous plate forming a filter element having a plurality of perforations extending there through, the plurality of perforations each disposed within a furrow and located radially about a central axis of the filter element, the furrow having a depth less than the plate thickness,
wherein the plurality of perforations each having a perforation length oriented along a line extending from the central axis to an outer edge of the simulated wellbore fracture; and
plugging the perforations with the loss circulation materials.

22. The method of claim 21 further comprising:
measuring an amount of filtrate passed through the plurality of perforations of the filter element.

23. The method of claim 21 further comprising:
engaging the filter element within the wellbore fluid testing apparatus to sealingly engage the filter element between an inlet of the testing apparatus and an outlet of the testing apparatus.

24. The method of claim 21, wherein the filter element further comprises:
a plurality of spacers depending away from a bottom face of the filter element, the spacers to provide support to the filter element.

25. The method of claim 21, wherein the filter element comprises a non-porous material selected from the group consisting of perforated ceramic plates, polycarbonate plates, metallic plates, and combinations thereof.

26. The method of claim 21 further comprising:
providing a cell body disposed within the wellbore fluid apparatus, the cell body with a lip to engage the filter element; and
providing a pressurization inlet to pressurize the cell body.

* * * * *